US012595175B2

(12) United States Patent
Ou et al.

(10) Patent No.: US 12,595,175 B2
(45) Date of Patent: *Apr. 7, 2026

(54) CALCIUM PHOSPHATE-BASED CORE-SHELL STRUCTURED MATERIAL, METHOD FOR PREPARING THE SAME, AND ORAL CARE COMPOSITION USING THE SAME

(71) Applicant: 3D GLOBAL BIOTECH INC., New Taipei City (TW)

(72) Inventors: Keng-Liang Ou, New Taipei City (TW); Chao-Hsuan Chen, Taipei City (TW); Chih-Hua Yu, Hualien County (TW); Yu-Hao Chan, Taipei City (TW); Wei-Jen Cheng, New Taipei City (TW)

(73) Assignee: 3D GLOBAL BIOTECH INC., New Taipei City (TW)

( * ) Notice: Subject to any disclaimer, the term of this patent is extended or adjusted under 35 U.S.C. 154(b) by 847 days.

This patent is subject to a terminal disclaimer.

(21) Appl. No.: 17/844,734

(22) Filed: Jun. 21, 2022

(65) Prior Publication Data

US 2022/0402760 A1 Dec. 22, 2022

(30) Foreign Application Priority Data

Jun. 21, 2021 (TW) ................................. 110122506

(51) Int. Cl.
| | |
|---|---|
| *C01B 25/32* | (2006.01) |
| *A61K 8/02* | (2006.01) |
| *A61Q 11/00* | (2006.01) |

(52) U.S. Cl.
CPC ............ *C01B 25/32* (2013.01); *A61K 8/0233* (2013.01); *A61Q 11/00* (2013.01);
(Continued)

(58) Field of Classification Search
CPC ..... C01B 25/32; C01B 25/327; A61K 8/0233; A61K 2800/805; A61K 2800/92;
(Continued)

(56) References Cited

U.S. PATENT DOCUMENTS

| | | | |
|---|---|---|---|
| 2010/0143271 | A1 | 6/2010 | Yang et al. |
| 2011/0059149 | A1 | 3/2011 | Little et al. |
| 2011/0150791 | A1 | 6/2011 | Yang et al. |

FOREIGN PATENT DOCUMENTS

| | | |
|---|---|---|
| CN | 1488680 A | 4/2004 |
| JP | 2014111554 A | 6/2014 |

(Continued)

OTHER PUBLICATIONS

Niu et al. (Sustained delivery of calcium and orthophosphate ions from amorphous calcium phosphate and poly(L-lactic acid)-based electrospinning nanofibrous scaffold, Nature, 2017) (Year: 2017).*

(Continued)

*Primary Examiner* — Anthony J Zimmer
*Assistant Examiner* — Logan Laclair
(74) *Attorney, Agent, or Firm* — Li & Cai Intellectual Property Office

(57) ABSTRACT

A calcium phosphate-based core-shell structured material, a method for preparing the same, and an oral care composition using the same are provided. The calcium phosphate-based core-shell structured material includes an amorphous calcium phosphate (ACP) core and a β-tricalcium phosphate (β-TCP) shell covering the core. The method includes a first sintering step and a second sintering step. The first sintering step is to sinter an ACP material at between 700° C. and 800° C. to obtain an α-TCP shell. The second sintering step allows the α-TCP shell to form into the β-TCP shell by sintering at between 800° C. and 900° C. The oral care composition includes a calcium phosphate mixture and an (Continued)

orally receivable carrier. The calcium phosphate mixture includes a powder of the calcium phosphate-based core-shell structured material and a tricalcium phosphate powder mixed in a weight ratio from 3:5 to 3:7.

8 Claims, 13 Drawing Sheets

(52) U.S. Cl.
 CPC .... *A61K 2800/805* (2013.01); *A61K 2800/92* (2013.01); *C01P 2004/34* (2013.01)

(58) Field of Classification Search
 CPC ........ A61K 2800/621; A61K 2800/651; A61K 8/0241; A61K 8/24; A61K 8/11; A61K 8/25; A61K 9/501; A61K 33/42; A61Q 11/00; C01P 2004/34; A61P 1/02
 See application file for complete search history.

(56) References Cited

FOREIGN PATENT DOCUMENTS

| KR | 100783587 B1 | 12/2007 |
| KR | 1020080069493 A | 7/2008 |
| KR | 101885880 B1 | 8/2018 |
| TW | 201021849 A1 | 6/2010 |
| TW | 201121576 A1 | 7/2011 |
| TW | 201221145 A1 | 6/2012 |
| WO | WO-2021189435 A1 * | 9/2021 | ............. A61L 27/40 |

OTHER PUBLICATIONS

Ke et al. (Enhancing the Osteogenic Capability of Core-Shell Bilayered Bioceramic Microspheres with Adjustable Biodegradation, ACS Applied Materials & Interfaces, 2017) (Year: 2017).*

Machine translation of WO-2021189435-A1 (Year: 2021).*

Chen Junyu, Du Qian,Liu Yan, Lu Yuezhi, Li Xiaoqing, "Research progress on remineralization materials based on calcium phosphate systems", Oral medicine, Dec. 2013 vol. 33 Issue 12, Dec. 7, 2013 (Dec. 28, 2013), pp. 855-858.

Ping-Jen Hou, Chang-Yu Lee, Keng-Liang Ou, Wen-Chien Lan, Yen-Chun Chuo, Hung-Yang Lin, Hsiao-Wei Chao, Bai-Hung Huang, Takashi Saito, Hain-Yu Tsai, Tzu-Sen Yang,Christopher J. Walinski and Muhammad Ruslin, "Calcium Release from Different Toothpastes after the Incorporation of Tricalcium Phosphate and Amorphous Calcium Phosphate", Appl. Sci. 2021, 11, 1848, p. 1-12, Published: Feb. 19, 2021.

* cited by examiner

CALCIUM PHOSPHATE-BASED CORE-SHELL STRUCTURED MATERIAL, METHOD FOR PREPARING THE SAME, AND ORAL CARE COMPOSITION USING THE SAME

CROSS-REFERENCE TO RELATED PATENT APPLICATION

This application claims the benefit of priority to Taiwan Patent Application No. 110122506, filed on Jun. 21, 2021. The entire content of the above identified application is incorporated herein by reference.

Some references, which may include patents, patent applications and various publications, may be cited and discussed in the description of this disclosure. The citation and/or discussion of such references is provided merely to clarify the description of the present disclosure and is not an admission that any such reference is "prior art" to the disclosure described herein. All references cited and discussed in this specification are incorporated herein by reference in their entireties and to the same extent as if each reference was individually incorporated by reference.

FIELD OF THE DISCLOSURE

The present disclosure relates to a calcium phosphate-based core-shell structured material, a method for preparing the same, and a composition using the same, and more particularly to a calcium phosphate-based core-shell structured material for oral care and remineralization, a method for preparing the same, and an oral care composition using the same.

BACKGROUND OF THE DISCLOSURE

The structure of a tooth includes enamel located on the surface of the dental crown, dentin as an inner layer, and pulp that is rich in nerves and blood vessels. Since the main component of both enamel and dentin is hydroxyapatite (HAP), both are highly calcified hard tissues.

In the oral environment, the phosphate and calcium ions between the liquid phase (saliva) and the solid phase (enamel) maintain a dynamic balance of demineralization and remineralization. However, the oral environment can change from neutral to acidic due to metabolites in the mouth, such that calcium phosphate (CaP) crystals on a tooth surface are dissolved under acidic conditions, causing a loss of calcium ions. When the oral environment returns to neutral from acidic, demineralization is halted and remineralization is carried out such that the free calcium ions and phosphate will re-enter the tooth surface to form CaP crystals.

It is well known that enamel consists of micron-sized calcium carbonate ($CaCO_3$) deficient hydroxyapatite (HAP) microcrystals, in which the main component (at about 97%) is hydroxyapatite (HAP). Recent studies have found that CaP, such as amorphous calcium phosphate (ACP), $\beta$-tricalcium phosphate ($\beta$-TCP), $\alpha$-tricalcium phosphate ($\alpha$-TCP) and hydroxyapatite (HAP), are similar to natural enamel and can be applied to oral care products.

In the remineralization process, calcium ions in the oral environment play an important role in facilitating formation of calcium phosphate inside the tooth. If amorphous calcium phosphate (ACP) has a better solubility, it can be an excellent source of calcium ions and phosphate ions. However, if amorphous calcium phosphate (ACP) is in contact with water in a physiological environment, it is easily converted into a low-solubility hydroxyapatite ($Ca_{10}(PO_4)_6(OH)_2$) through phase transition. In addition, if calcium ions and phosphate ions dissolved from amorphous calcium phosphate (ACP) cannot stay for long enough in the mouth or on the tooth surface, the remineralization effect cannot be fully carried out thereby. $\beta$-tricalcium phosphate ($\beta$-TCP) is a tricalcium phosphate that is considered to be stable at room temperature, but its calcium ion content is lower than that of amorphous calcium phosphate (ACP).

Therefore, how to improve remineralization materials, so as to overcome the above-mentioned inadequacies, has become one of the important issues to be addressed in the industry.

SUMMARY OF THE DISCLOSURE

In response to the above-referenced technical inadequacies, the present disclosure provides a calcium phosphate-based core-shell structured material, a preparing method thereof, and applications thereof.

In one aspect, the present disclosure provides a calcium phosphate-based core-shell structured material, which includes an amorphous calcium phosphate (ACP) core and a $\beta$-tricalcium phosphate ($\beta$-TCP) shell covering the amorphous calcium phosphate (ACP) core.

In one embodiment of the present disclosure, the calcium phosphate-based core-shell structured material is prepared by the following steps: a first sintering step that includes sintering an amorphous calcium phosphate (ACP) material to produce the amorphous calcium phosphate (ACP) core and an $\alpha$-tricalcium phosphate ($\alpha$-TCP) shell; and a second sintering step including sintering the $\alpha$-tricalcium phosphate ($\alpha$-TCP) shell to form the $\beta$-tricalcium phosphate ($\beta$-TCP) shell.

In one embodiment of the present disclosure, the first sintering step is performed at a predetermined temperature between 700° C. and 800° C. for 1 hour by heating at a temperature rising rate of 3° C./min. The second sintering step is performed at a predetermined temperature between 800° C. and 900° C. for 1 to 2 hours.

In one embodiment of the present disclosure, after the second sintering step, a heat treatment is performed at a predetermined temperature for 1 hour by heating at a temperature raising rate of 5° C./min.

In another aspect, the present disclosure provides a method for preparing a calcium phosphate-based core-shell structured material, which includes: providing an amorphous calcium phosphate (ACP) material; and subjecting the amorphous calcium phosphate (ACP) material to a sintering process. The sintering process includes: a first sintering step which includes sintering the amorphous calcium phosphate (ACP) material at a predetermined temperature from 700° C. to 800° C. to obtain an $\alpha$-tricalcium phosphate ($\alpha$-TCP) shell; and a second sintering step which includes sintering the amorphous calcium phosphate (ACP) material at a predetermined temperature from 800° C. to 900° C. to allow the $\alpha$-tricalcium phosphate ($\alpha$-TCP) shell to form into a $\beta$-tricalcium phosphate ($\beta$-TCP) shell.

In one embodiment of the present disclosure, the method further includes, after the second sintering step, heating the material to a predetermined temperature at a temperature raising rate of 5° C./min and maintaining the predetermined temperature for 1 hour.

In yet another aspect, the present disclosure provides an oral care composition, which includes a calcium phosphate mixture and an orally acceptable carrier. The calcium phosphate mixture includes a powder of a calcium phosphate-based core-shell structured material as described in the present disclosure and a tricalcium phosphate powder. The powder of the calcium phosphate-based core-shell structured material and the tricalcium phosphate powder are mixed in a weight ratio from 3:5 to 3:7.

In one embodiment of the present disclosure, the oral care composition is used in applications such as a toothpaste, dental powder, tooth cleaning solution, mouthwash, mousse, denture product, topical oral gel, oral tablet, buccal tablet, sugar coated tablet, chewing gum, tooth patch, or artificial dental brace.

In one embodiment of the present disclosure, the oral care composition is added in an amount between 10 wt % and 35 wt % in the applications.

In one embodiment of the present disclosure, the tricalcium phosphate powder is formed by sintering at a predetermined temperature between 700° C. and 1500° C.

In one embodiment of the present disclosure, the tricalcium phosphate powder is formed by a first sintering step and a second sintering step. The first sintering step is performed at a temperature of 800° C. for 1 hour by heating at a temperature raising rate of 3° C./min, and the second sintering step is performed at a predetermined temperature between 1100° C. and 1200° C. for 1 to 3 hours by heating at a temperature raising rate of 5° C./min.

Therefore, in the calcium phosphate-based core-shell structured material, the method for preparing the same, and the oral care composition using the same provided by the present disclosure, by virtue of "the β-tricalcium phosphate (β-TCP) shell covering the amorphous calcium phosphate (ACP) core," the stability of the calcium phosphate-based core-shell structured material can be improved and a better release rate of calcium ions can be achieved, thereby increasing a free calcium ion concentration in an aqueous solution.

These and other aspects of the present disclosure will become apparent from the following description of the embodiment taken in conjunction with the following drawings and their captions, although variations and modifications therein may be affected without departing from the spirit and scope of the novel concepts of the disclosure.

BRIEF DESCRIPTION OF THE DRAWINGS

The described embodiments may be better understood by reference to the following description and the accompanying drawings, in which.

DETAILED DESCRIPTION OF THE EXEMPLARY EMBODIMENTS

Figures 1, 2:
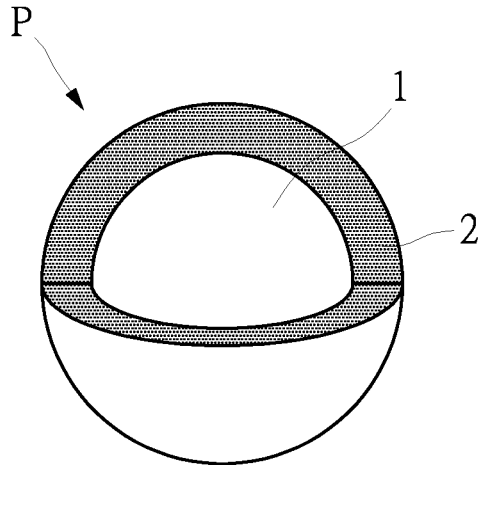
FIG. 1 is a partial schematic view of a calcium phosphate-based core-shell structured material of the present disclosure.
FIG. 2 is a schematic view showing free calcium ions released from the calcium phosphate-based core-shell structured material of the present disclosure.

The present disclosure is more particularly described in the following examples that are intended as illustrative only since numerous modifications and variations therein will be apparent to those skilled in the art. Like numbers in the drawings indicate like components throughout the views. As used in the description herein and throughout the claims that follow, unless the context clearly dictates otherwise, the meaning of "a", "an", and "the" includes plural reference, and the meaning of "in" includes "in" and "on". Titles or subtitles can be used herein for the convenience of a reader, which shall have no influence on the scope of the present disclosure.

The terms used herein generally have their ordinary meanings in the art. In the case of conflict, the present document, including any definitions given herein, will prevail. The same thing can be expressed in more than one way. Alternative language and synonyms can be used for any term(s) discussed herein, and no special significance is to be placed upon whether a term is elaborated or discussed herein. A recital of one or more synonyms does not exclude the use of other synonyms. The use of examples anywhere in this specification including examples of any terms is illustrative only, and in no way limits the scope and meaning of the present disclosure or of any exemplified term. Likewise, the present disclosure is not limited to various embodiments given herein. Numbering terms such as "first", "second" or "third" can be used to describe various components, signals or the like, which are for distinguishing one component/signal from another one only, and are not intended to, nor should be construed to impose any substantive limitations on the components, signals or the like.

First Embodiment

Referring to FIG. 1, a specific embodiment of the present disclosure provides a calcium phosphate-based core-shell structured material P, which includes an amorphous calcium phosphate (ACP) core 1 and a β-tricalcium phosphate (β-TCP) shell 2 covering the amorphous calcium phosphate (ACP) core 1.

Referring to FIG. 2, the calcium phosphate-based core-shell structured material P can perform a two-stage process for releasing calcium ions. Firstly, the β-tricalcium phosphate (β-TCP) shell 2 releases free calcium ions in an aqueous solution. After the β-tricalcium phosphate (β-TCP) shell 2 finished releasing free calcium ions, the amorphous calcium phosphate (ACP) core 1 can be exposed from the β-tricalcium phosphate (β-TCP) shell 2 to release calcium ions. Therefore, an improved release rate of calcium ions can be achieved, thereby increasing a free calcium ion concentration in an aqueous solution.

Figure 3:
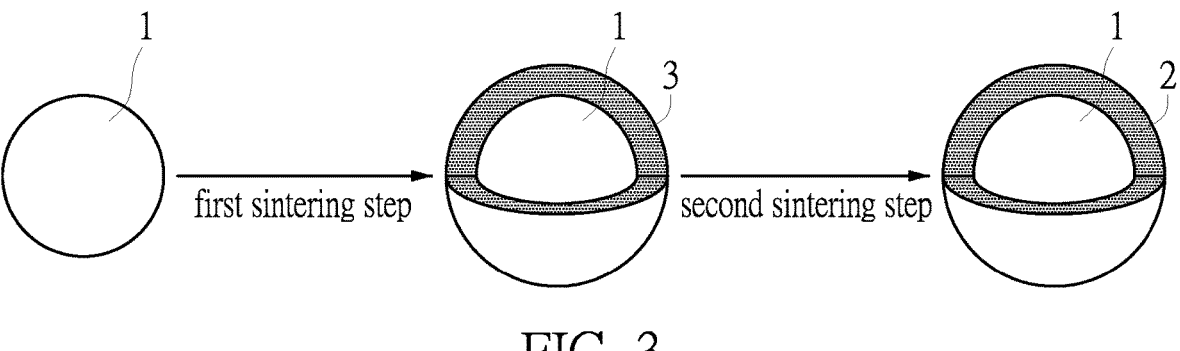
FIG. 3 is a schematic view showing a sintering process of the calcium phosphate-based core-shell structured material of the present disclosure.

The calcium phosphate-based core-shell structured material P is obtained by subjecting an amorphous calcium phosphate (ACP) material to a sintering process. The sintering process allows the amorphous calcium phosphate (ACP) material to produce the β-tricalcium phosphate (β-TCP) shell 2 covering the amorphous calcium phosphate (ACP) core 1. More specifically, as shown in FIG. 3, a first sintering step allows the amorphous calcium phosphate (ACP) material to produce an α-tricalcium phosphate (α-TCP) shell 3, and a second sintering step allows the α-tricalcium phosphate (α-TCP) shell 3 to form into a β-tricalcium phosphate (β-TCP) shell 2.

As described in further detail below, in the two-step sintering process of the amorphous calcium phosphate (ACP) material, the first sintering step is performed at a predetermined temperature between 700° C. and 800° C. for 1 hour by heating at a temperature raising rate of 3° C./min, and the second sintering step is performed at a predetermined temperature between 800° C. and 900° C. for 1 to 2 hours by heating at a gradient rate of 5° C./min.

Figure 4:
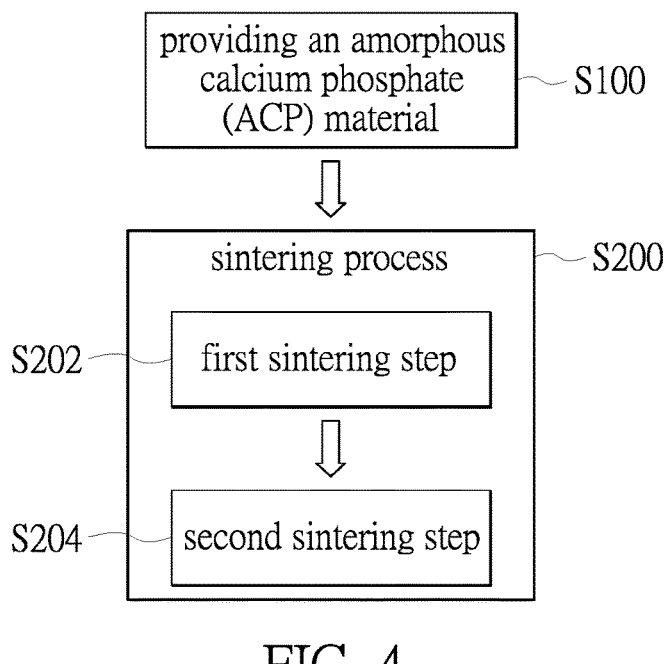
FIG. 4 is a flowchart of a method for preparing the calcium phosphate-based core-shell structured material of the present disclosure.

Reference is made to FIG. 4. A method for preparing a calcium phosphate-based core-shell structured material of the present disclosure includes: step S100, providing an amorphous calcium phosphate (ACP) material; and step S200, subjecting the amorphous calcium phosphate (ACP) material to a sintering process. The sintering process includes: step S202 (i.e., the first sintering step), sintering the amorphous calcium phosphate (ACP) material at a predetermined temperature of 700-800° C. to obtain an α-tricalcium phosphate (α-TCP) shell; and step S204 (i.e., the second sintering step), sintering the amorphous calcium phosphate (ACP) material at a predetermined temperature of 800-900° C. to allow the α-tricalcium phosphate (α-TCP) shell to form into the β-tricalcium phosphate (β-TCP) shell.

In addition, step S206 (not shown in the figures) of heating the material to a predetermined temperature at a temperature raising rate of 5° C./min and maintaining the temperature for 1 hour is further included.

The present disclosure further provides an oral care composition, which includes a calcium phosphate mixture and an orally receivable carrier. The calcium phosphate mixture includes a powder of a calcium phosphate-based core-shell structured material as described in the present disclosure and a tricalcium phosphate powder. The powder of the calcium phosphate-based core-shell structured material and the tricalcium phosphate powder are mixed in a weight ratio from 3:5 to 3:7. More preferably, in the calcium phosphate mixture, the powder of the calcium phosphate-based core-shell structured material and the tricalcium phosphate powder are mixed in a weight ratio of 3:6 (i.e., 1:2).

The orally receivable carrier can be a substance used in oral care compositions in the related art, which is exemplified by a solvent, an anti-calculus agent, a buffer, a grinding or polishing substance, a teeth-whitening agent, a teeth-bleaching agent, an alkali metal bicarbonate, a thickening substance, a humectant, a surfactant, titanium dioxide, a flavoring agent, a sweetener, xylitol, a colorant, or any combination thereof.

Preferably, the oral care composition is applied to a liquid solution for rinsing, mouthwashing or spraying and powder, paste and gel products. The oral care composition is preferably added in an oral care product such as a toothpaste, dental powder, tooth cleaning solution, mouthwash, mousse, denture product, topical oral gel, oral tablet, buccal tablet, sugar coated tablet, chewing gum, tooth patch, or artificial dental brace in an amount between 10 wt % and 35 wt %, based on a total weight of the oral care product.

In one embodiment of the present disclosure, the oral care composition is added in a toothpaste in an amount of 10 wt %, based on a total weight of the toothpaste. In another one embodiment of the present disclosure, the oral care composition is added in a toothpaste in an amount of 25 wt %, based on a total weight of the toothpaste.

In one embodiment of the present disclosure, the oral care composition is mixed with a commonly available agent in a content between 10 wt % and 25 wt % of a total weight to prepare a suitable formulation, which is used for being coated on an artificial dental brace.

The tricalcium phosphate powder of the calcium phosphate mixture is formed by sintering at a predetermined temperature between 700° C. and 1500° C. More specifically, the tricalcium phosphate powder is formed by a two-step sintering process, in which a first sintering step is performed at a predetermined temperature of 800° C. for 1 hour by heating at a temperature raising rate of 3° C./min, and a second sintering step is performed at a predetermined temperature between 1100° C. and 1200° C. for 1 to 3 hours by heating at a temperature raising rate of 5° C./min. The sintered tricalcium phosphate powder exhibits an excellent stability.

Hereinafter, specific examples of the present disclosure will be further described with an experimental study of the present disclosure. However, such examples of the present disclosure are for exemplary purposes only and are not intended to limit the present disclosure.

[Sintering Preparation]

Amorphous calcium phosphate (ACP, commercially available from Popeye Marine Biotechnology Co., Ltd.) is subjected to a two-step sintering process in a heating furnace. A first sintering step is performed at a predetermined temperature of 700° C. for 1 hour, and a second sintering step is performed at a predetermined temperature between 800° C. and 900° C. for 1 to 2 hours by heating at a gradient rate of 5° C./min.

Tricalcium phosphate (TCP, commercially available from Popeye Marine Biotechnology Co., Ltd.) is subjected to a two-step sintering process in a heating furnace. A first sintering step is performed such that samples are heated to a predetermined temperature of 800° C. at a temperature raising rate of 3° C./min and maintained for 1 hour. Afterwards, a second sintering step is performed at a predetermined temperature between 1100° C. and 1200° C., in which the temperature is achieved by heating at a gradient rate of 5° C./min and maintained for 1, 2 or 3 hours, respectively.

[Analysis and Test]

Figure 5A:
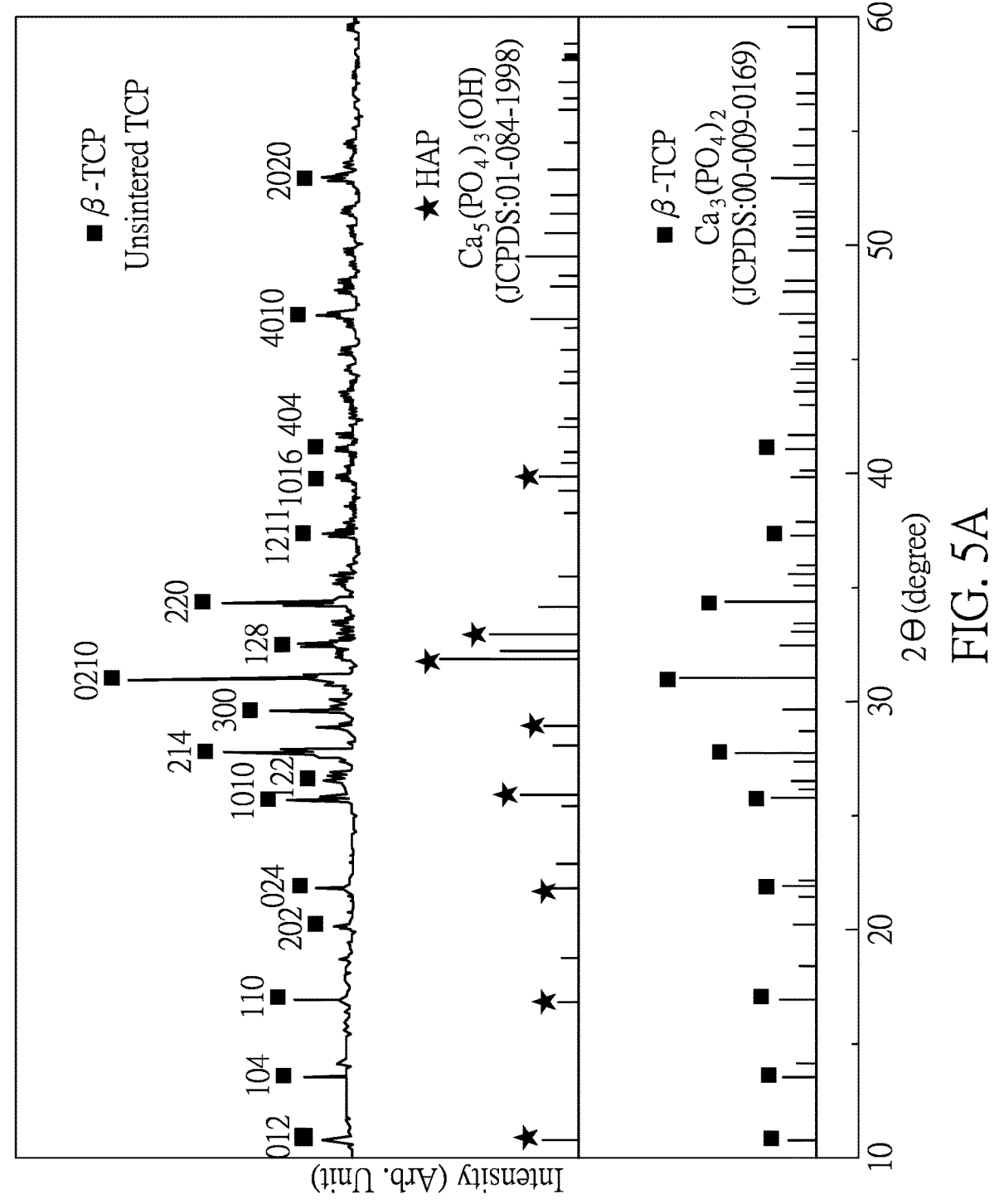
FIG. 5A is an X-ray diffraction diagram of unsintered tricalcium phosphate (TCP) of the present disclosure.
Figure 5B:
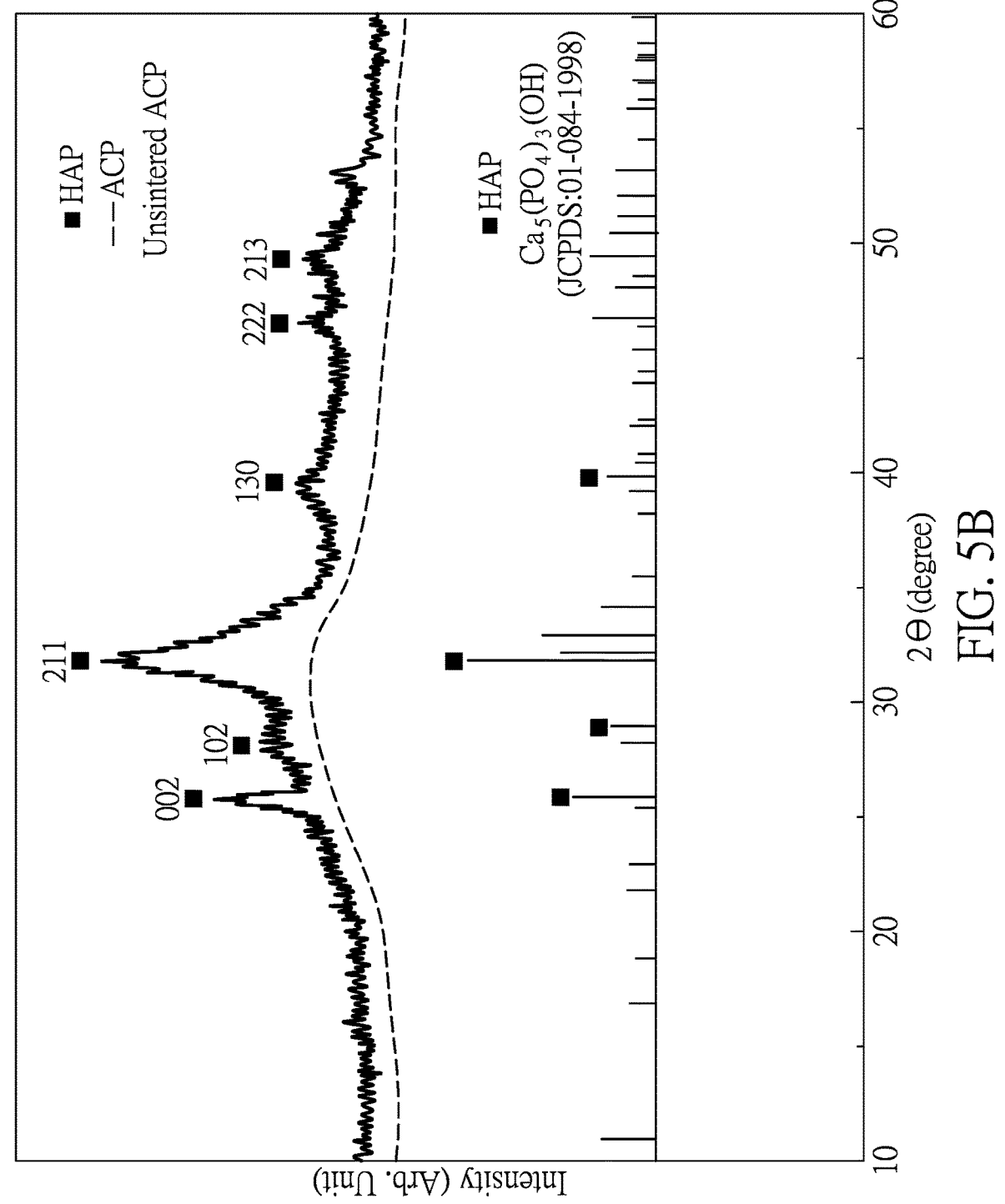
FIG. 5B is an X-ray diffraction diagram of unsintered amorphous calcium phosphate (ACP) of the present disclosure.

X-ray diffraction (XRD) analysis: an X-ray diffraction instrument (Model No. 200, Rigaku Co.) is used to identify unsintered tricalcium phosphate (TCP) and unsintered amorphous calcium phosphate (ACP), the results of which are shown in FIG. 5A and FIG. 5B.

7
8

Figure 6A:
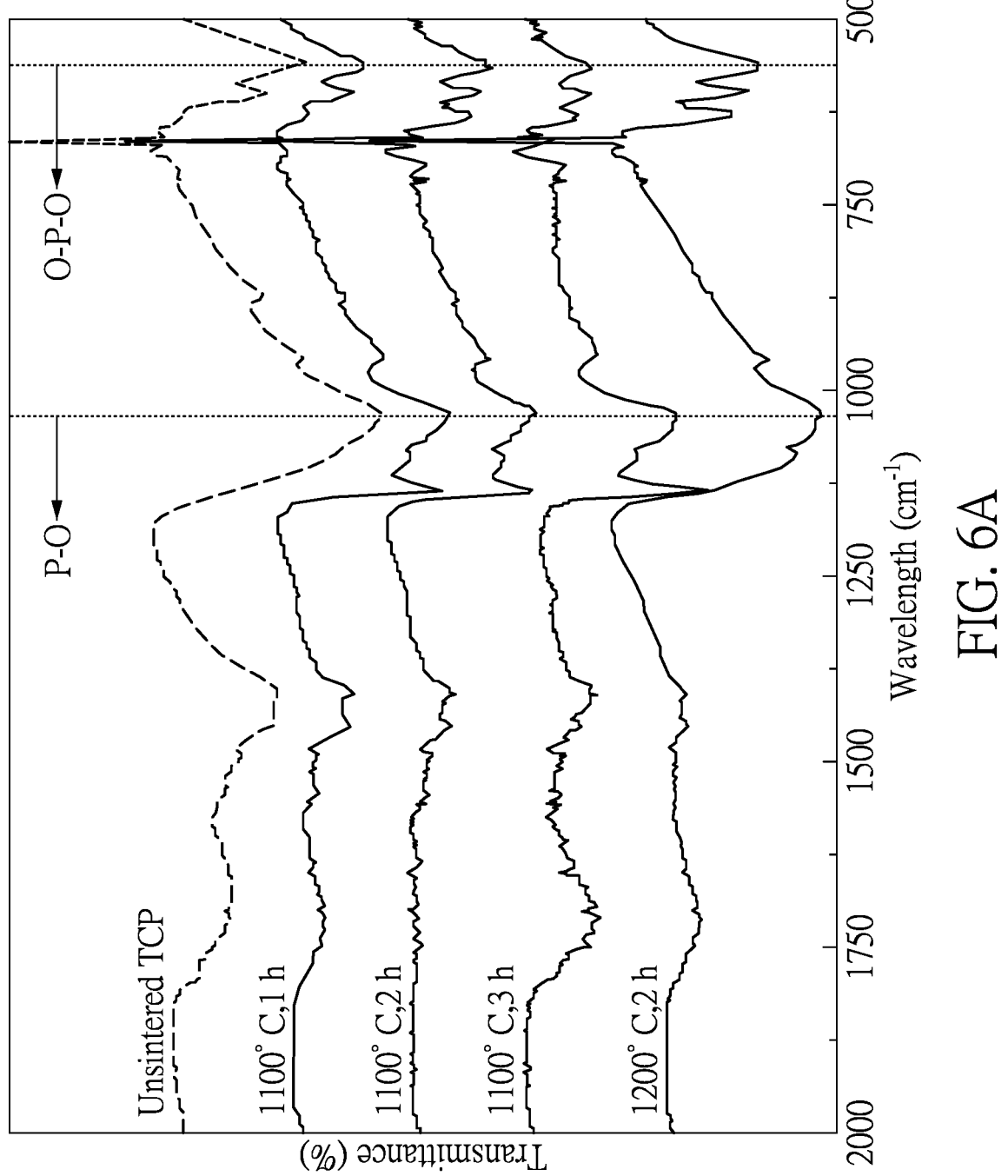
FIG. 6A shows Fourier transform infrared spectra of unsintered tricalcium phosphate (TCP) and sintered tricalcium phosphate (TCP) of different temperatures and times of the present disclosure.
Figure 6B:
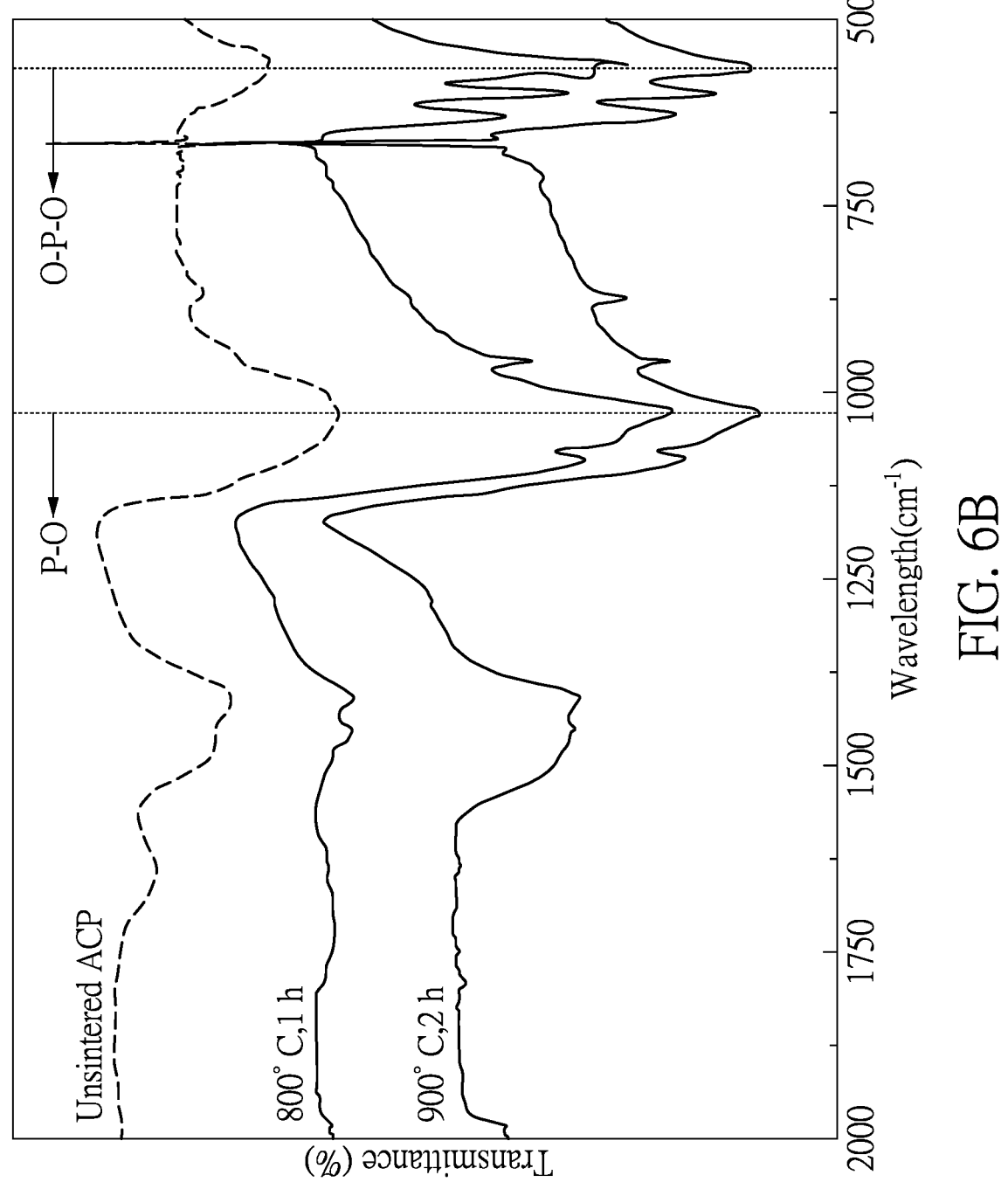
FIG. 6B shows Fourier transform infrared spectra of unsintered amorphous calcium phosphate (ACP) and sintered amorphous calcium phosphate (ACP) of different temperatures and times of the present disclosure.

Fourier transform infrared (FTIR) spectra: FIG. 6A and FIG. 6B show effects of different heat treatment temperatures and times on sample structures in preparation examples of sintered tricalcium phosphate (TCP) powders and sintered amorphous calcium phosphate (ACP) powders. FIG. 6A sequentially shows an unsintered TCP powder, TCP powders sintered at 1100° C. for 1, 2 and 3 hours respectively, and a TCP powder sintered at 1200° C. for 1 hour. It can be seen that, TCP can be stably generated under such temperature and time conditions. FIG. 6B sequentially shows an unsintered ACP powder, an ACP powder sintered at 800° C. for 1 hour, and an ACP powder sintered at 900° C. for 2 hours. It can be seen that the characteristic peak of $PO_4^{3-}$ increases significantly at 1100 $cm^{-1}$, which means that amorphous calcium phosphate (ACP) is transformed into $\alpha$-tricalcium phosphate ($\alpha$-TCP) and $\beta$-tricalcium phosphate ($\beta$-TCP) under 800° C. and 900° C.

Figure 7A:
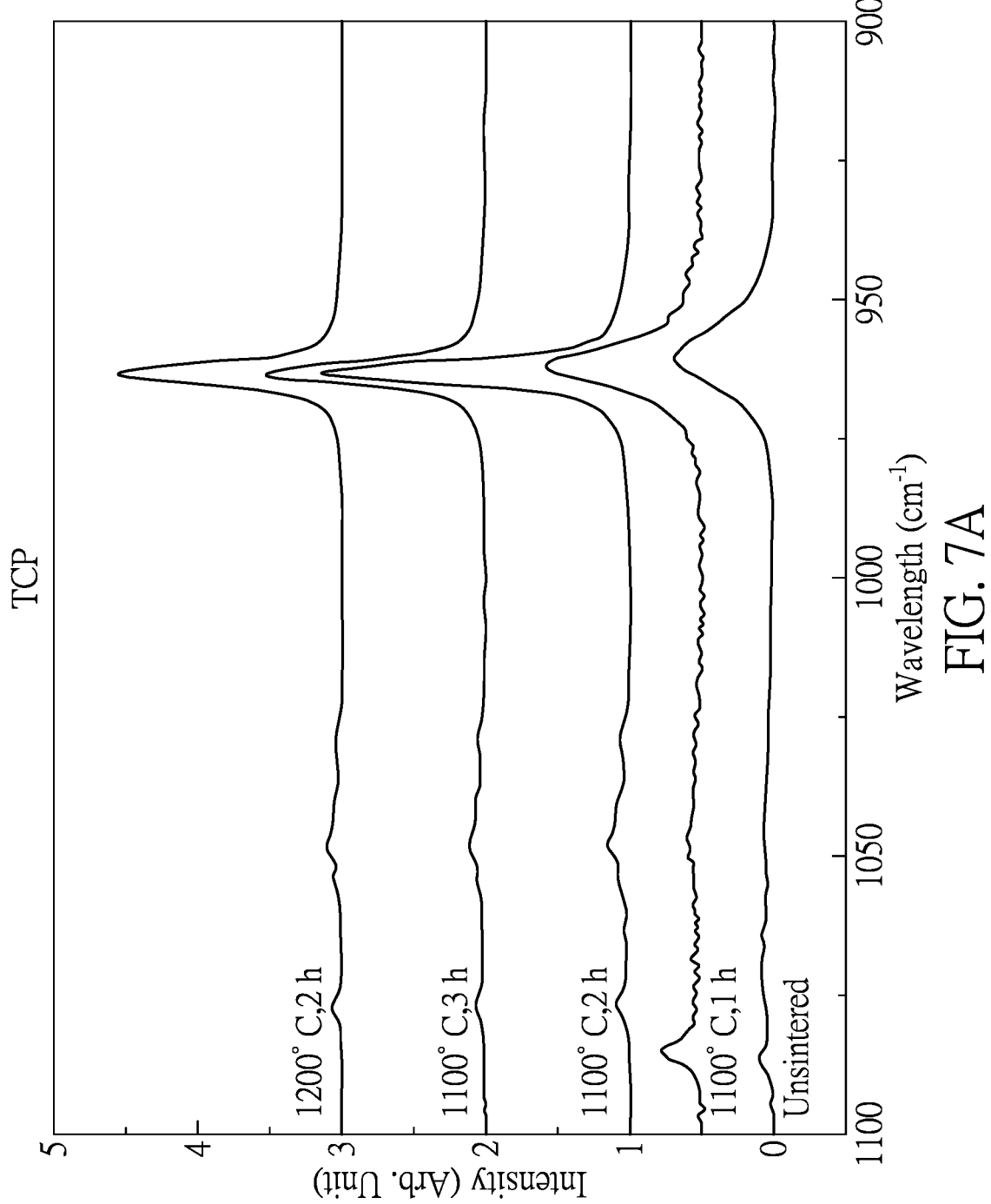
FIG. 7A shows a Raman spectrum of tricalcium phosphate (TCP) of the present disclosure.
Figure 7B:
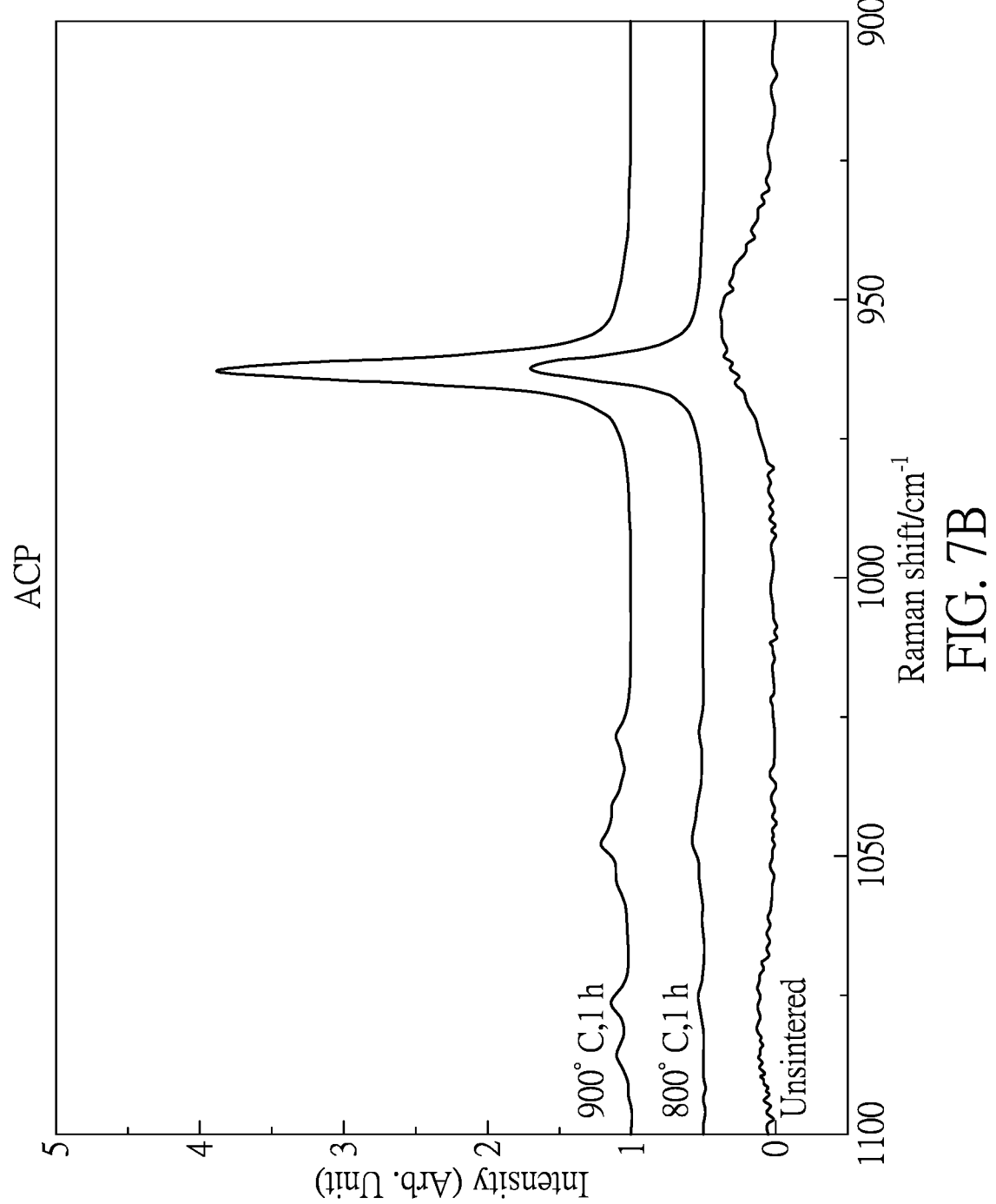
FIG. 7B shows a Raman spectrum of amorphous calcium phosphate (ACP) of the present disclosure.

Raman spectra: FIG. 7A and FIG. 7B show Raman spectra of sintered tricalcium phosphate (TCP) powders and sintered amorphous calcium phosphate (ACP) powders of preparation examples. It can be seen that the characteristic peak of $PO_4^{3-}$ in a symmetric stretching mode appears at a wavelength of 960 $cm^{-1}$, and has a higher wavenumber (v) and a narrower half width (W½) as the temperature and heat treatment time increases.

Figure 7C:
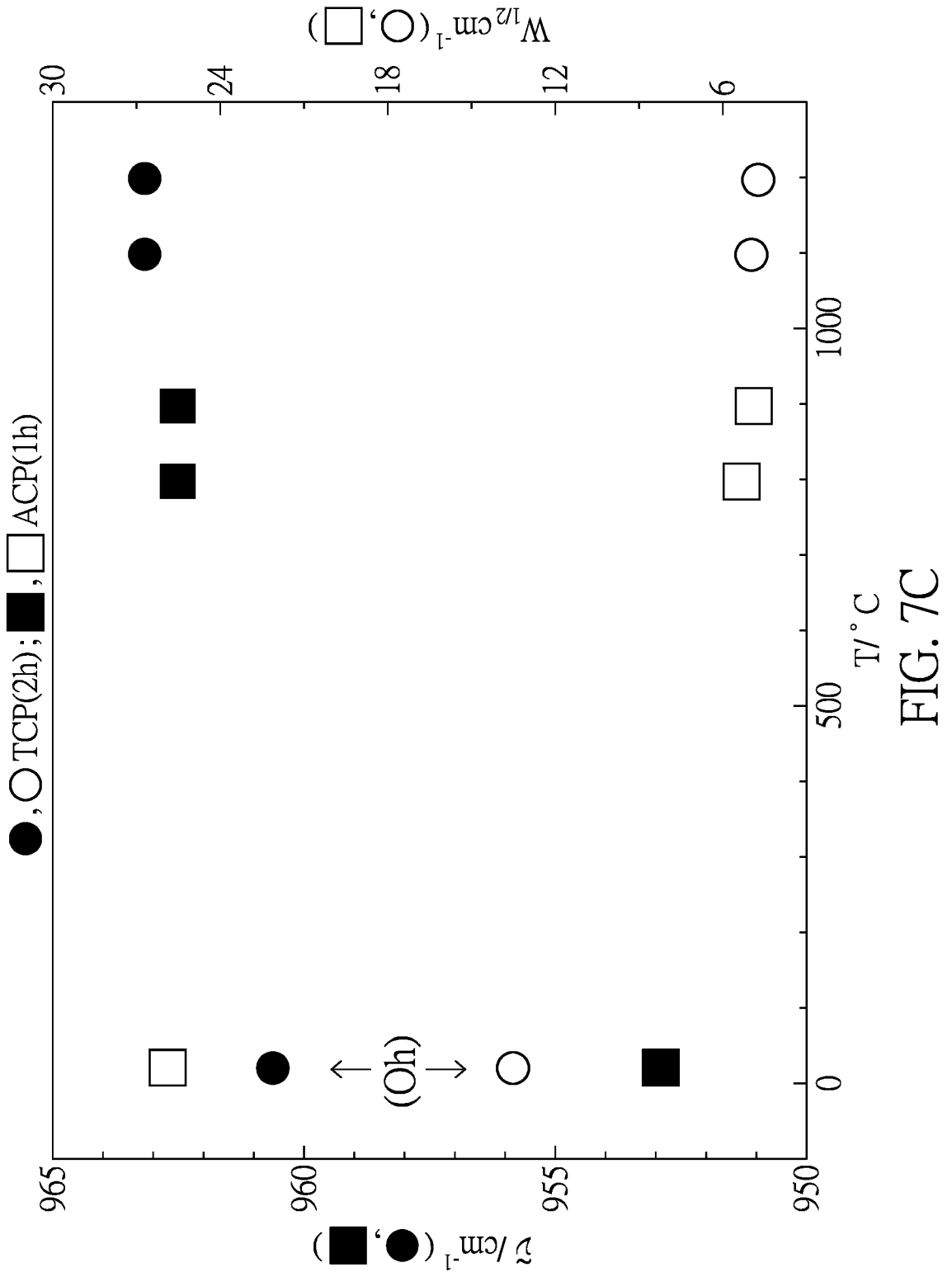
FIG. 7C shows a crystallinity analysis of sintered amorphous calcium phosphate (ACP) of the present disclosure.
Figure 7D:
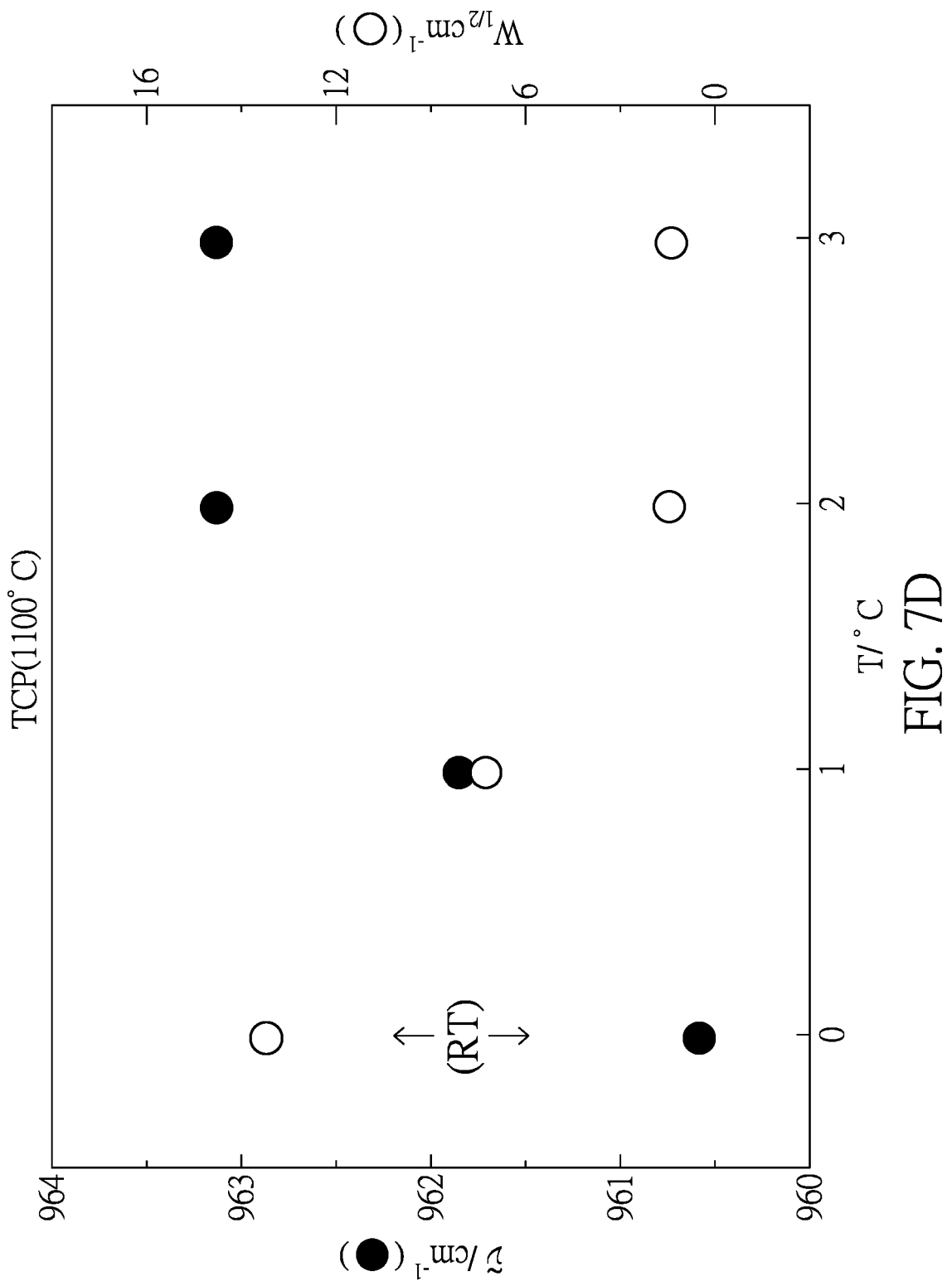
FIG. 7D shows a crystallinity analysis of sintered tricalcium phosphate (TCP) of the present disclosure.

Crystallinity analysis: as shown in FIG. 7C and FIG. 7D, a heat treatment after sintering not only promotes the whitening toothpaste (Colgate-Palmolive Company, USA), a BORONIA herbal whitening toothpaste (BORONIA, Taiwan), and a BioMin F toothpaste (BioMin Technologies Limited, UK), which are marked according to respective brand names.

Comparative Examples

A sintered TCP powder is respectively added to each of commercially available toothpastes and respectively in different ratios of 0%, 10% and 25% for testing free calcium ion release.

The toothpastes are respectively a Nano-Bio toothpaste (Pac-Dent Inc., USA), a Colgate full-effect professional whitening toothpaste (Colgate-Palmolive Company, USA), a BORONIA herbal whitening toothpaste (BORONIA, Taiwan), and a BioMin F toothpaste (BioMin Technologies Limited, UK), which are marked according to respective brand names.

Figure 9A:
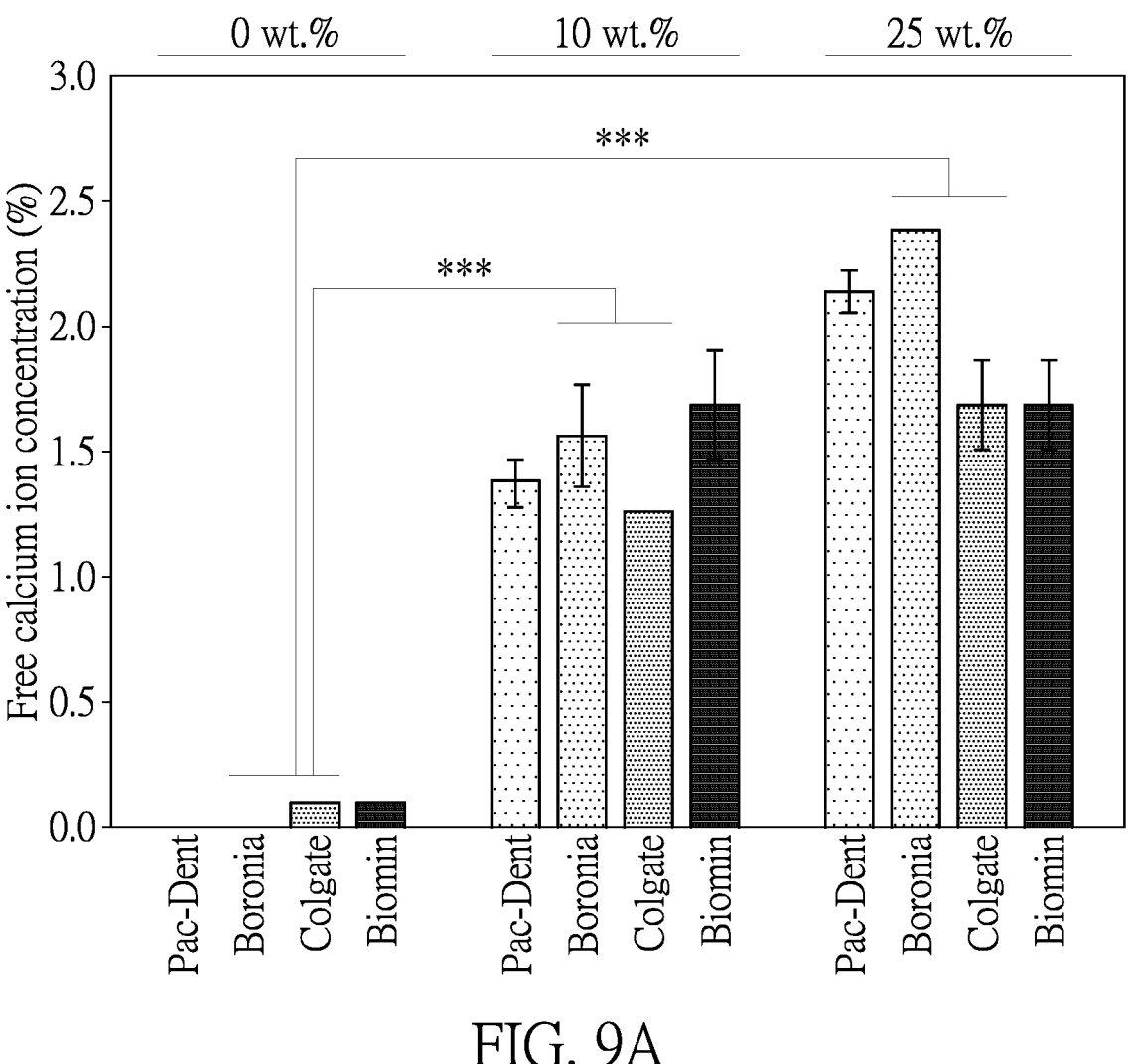
FIG. 9A is a chart showing calcium ion release concentrations of Comparative Examples of the present disclosure.
Figure 9B:
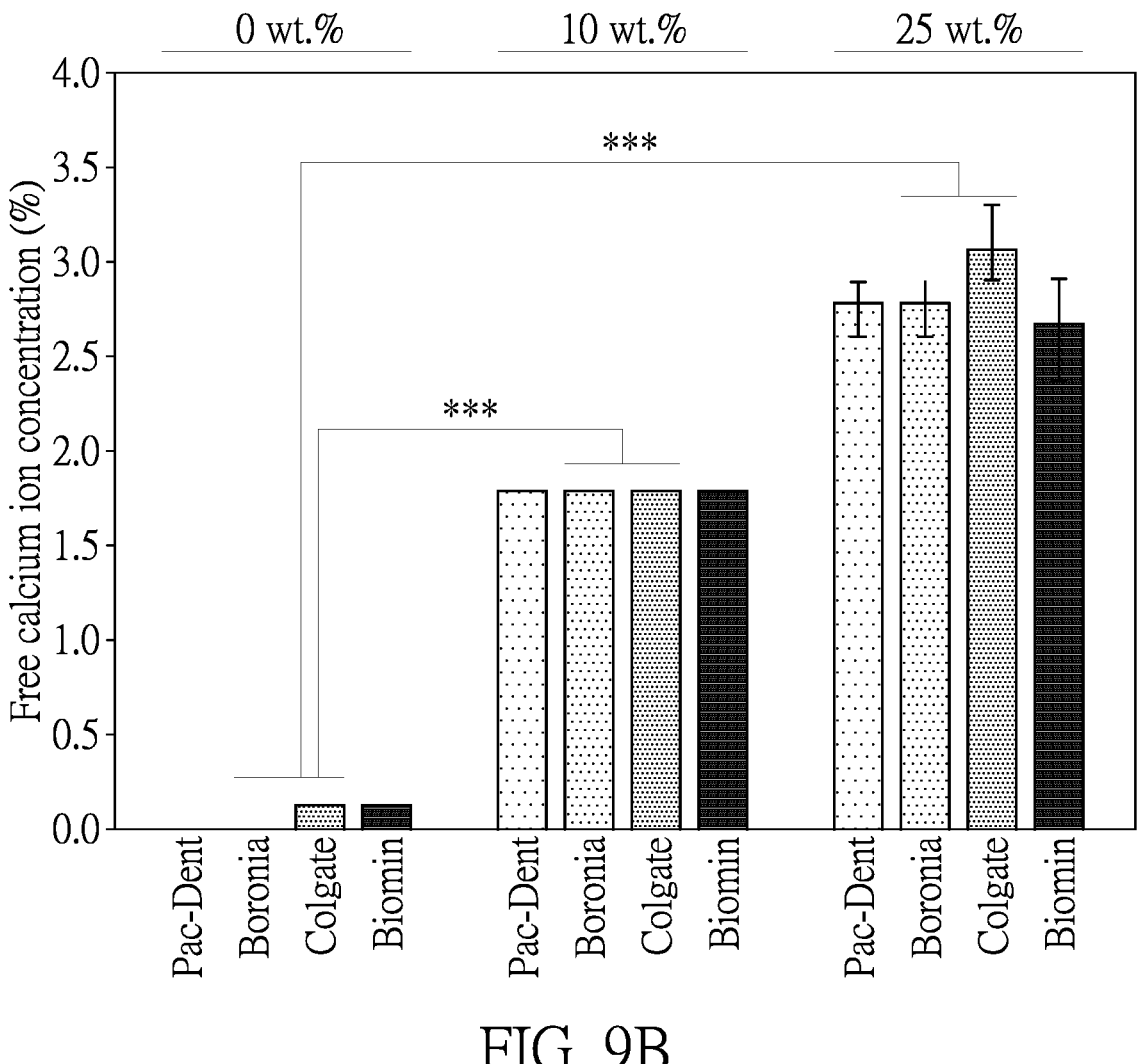
FIG. 9B is a chart showing calcium ion release concentrations of Examples of the present disclosure.

The test results of calcium ion release concentrations of examples and comparative examples are recorded in Table 1, FIG. 9A and FIG. 9B.

The calcium ion concentrations of samples in accordance with examples and comparative examples are measured by titration of ethylenediaminetetraacetic acid (EDTA, Sigma Aldrich, Taiwan).

TABLE 1

| | Contents | | | | | |
|---|---|---|---|---|---|---|
| | Examples | | | Comparatives Examples | | |
| Toothpastes | 0 wt % | 10 wt % | 25 wt % | 0 wt % | 10 wt % | 25 wt % |
| Nano-Bio | 0 | 1.8 | 2.79 ± 0.17 | 0 | 1.38 ± 0.10 | 2.14 ± 0.07 |
| Colgate | 0 | 1.8 | 2.79 ± 0.17 | 0 | 1.56 ± 0.21 | 2.39 |
| BORONIA | 0.10 | 1.8 | 3.09 ± 0.17 | 0.10 | 1.26 ± 0 | 1.69 ± 0.17 |
| BioMin F | 0.11 | 1.8 | 2.69 ± 0.30 | 0.11 | 1.69 ± 0.21 | 1.69 ± 0.17 | formation of TCP, but also allows amorphous calcium phosphate (ACP) to transform into $\alpha$-tricalcium phosphate ($\alpha$-TCP) and $\beta$-tricalcium phosphate ($\beta$-TCP), which can also increase crystal strength to achieve a higher crystallinity.

[Free Calcium Ion Concentration Test at Different pH Values]

Figure 8:
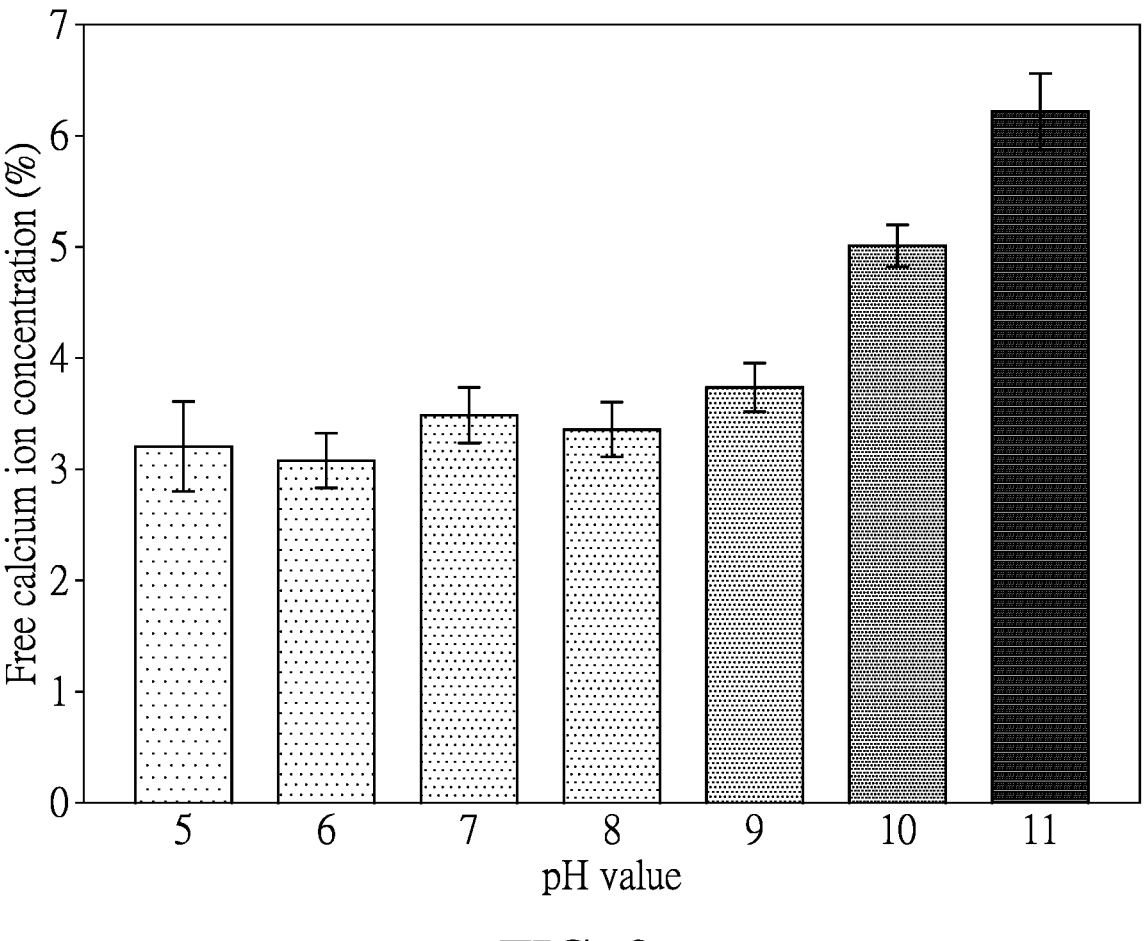
FIG. 8 is a test chart showing free calcium ion concentrations of an oral care composition of the present disclosure at different pH values.

As shown in FIG. 8, a sintered tricalcium phosphate (TCP) powder and an ACP powder having a $\beta$-tricalcium phosphate ($\beta$-TCP) shell of preparation examples are mixed in a ratio of 2:1 for testing free calcium ion release rates at different pH values. A stable releasing amount is exhibited in the range from pH 5 to 9, and an average free calcium ion concentration is 3.4%, thereby meeting the pH of consumer goods such as toothpaste. A free calcium ion concentration increases significantly to 5.0% and 6.2% at pH 10 and 11, which is caused by residual calcium oxide in a sintering process.

Examples

A sintered TCP powder and an ACP powder of preparation examples are mixed in a ratio of 2:1. The resulting mixture is added to each of commercially available toothpastes and respectively in different ratios of 0%, 10% and 25% for testing free calcium ion release.

The toothpastes are respectively a Nano-Bio toothpaste (Pac-Dent Inc., USA), a Colgate full-effect professional Beneficial Effects of the Embodiments One of the beneficial effects of the calcium phosphate-based core-shell structured material, the method for preparing the same, and the oral care composition using the same provided by the present disclosure is that, by virtue of "the $\beta$-tricalcium phosphate ($\beta$-TCP) shell covering the amorphous calcium phosphate (ACP) core," the stability of the calcium phosphate-based core-shell structured material can be improved and a better release rate of calcium ions can be achieved, thereby increasing a free calcium ion concentration in an aqueous solution.

Furthermore, the $\beta$-tricalcium phosphate ($\beta$-TCP) shell can be produced from the amorphous calcium phosphate (ACP) material by a sintering process. When the amorphous calcium phosphate (ACP) material that has a core-shell structure is in an aqueous solution, the $\beta$-tricalcium phosphate ($\beta$-TCP) shell can release free calcium ions. After the $\beta$-tricalcium phosphate ($\beta$-TCP) shell finishes releasing free calcium ions, the amorphous calcium phosphate (ACP) core can be exposed from the $\beta$-tricalcium phosphate ($\beta$-TCP) shell to release calcium ions continuously or simultaneously.

Compared with a conventional TCP material, the oral care composition of the present disclosure which includes a mixture of the powder of the calcium phosphate-based core-shell structured material and the tricalcium phosphate powder has an improved calcium ion release rate and calcium ion content. Further, the oral care composition exhibits a stable releasing amount of free calcium at a range from pH 5 to 9 in which an average free calcium ion concentration is 3.4%. That is, in a general oral application of a weak alkaline state, an excellent releasing amount can be provided.

In more detail, the present disclosure also proves that, in comparison to only adding TCP, a higher free calcium ion concentration can be achieved by adding the oral care composition to a commercially available toothpaste.

The foregoing description of the exemplary embodiments of the disclosure has been presented only for the purposes of illustration and description and is not intended to be exhaustive or to limit the disclosure to the precise forms disclosed. Many modifications and variations are possible in light of the above teaching.

The embodiments were chosen and described in order to explain the principles of the disclosure and their practical application so as to enable others skilled in the art to utilize the disclosure and various embodiments and with various modifications as are suited to the particular use contemplated. Alternative embodiments will become apparent to those skilled in the art to which the present disclosure pertains without departing from its spirit and scope.

What is claimed is:

1. A calcium phosphate-based core-shell structured material, comprising:
   an amorphous calcium phosphate (ACP) core; and
   a β-tricalcium phosphate (β-TCP) shell covering the amorphous calcium phosphate core,
   wherein the calcium phosphate-based core-shell structured material is prepared by the following steps:
   a first sintering step including sintering an amorphous calcium phosphate (ACP) material to produce the amorphous calcium phosphate core and an α-tricalcium phosphate (α-TCP) shell, and a second sintering step including sintering the α-tricalcium phosphate (α-TCP) shell to form the β-tricalcium phosphate (β-TCP) shell, and
   wherein the first sintering step is performed at a predetermined temperature between 700° C. and 800° C. for 1 hour by heating at a temperature rising rate of 3° C./min, and the second sintering step is performed at a predetermined temperature between 800° C. and 900° C. for 1 to 2 hours.

2. The calcium phosphate-based core-shell structured material according to claim 1, wherein, after the second sintering step, a heat treatment is performed at a predetermined temperature for 1 hour by heating at a temperature raising rate of 5° C./min.

3. A method for preparing a calcium phosphate-based core-shell structured material, comprising:
   providing an amorphous calcium phosphate (ACP) material; and
   subjecting the amorphous calcium phosphate (ACP) material to a sintering process, so as to obtain an amorphous calcium phosphate (ACP) core and a β-tricalcium phosphate (β-TCP) shell, wherein the sintering process includes:
   a first sintering step: sintering the amorphous calcium phosphate (ACP) material at a predetermined temperature from 700° C. to 800° C. to obtain an α-tricalcium phosphate (α-TCP) shell; and
   a second sintering step: sintering the amorphous calcium phosphate (ACP) material at a predetermined temperature from 800° C. to 900° C. to allow the α-tricalcium phosphate (α-TCP) shell to form into the β-tricalcium phosphate (β-TCP) shell.

4. The method according to claim 3, further comprising: after the second sintering step, heating the material to a predetermined temperature at a temperature raising rate of 5° C./min and maintaining the predetermined temperature for 1 hour.

5. An oral care composition, comprising:
   a calcium phosphate mixture including a powder of a calcium phosphate-based core-shell structured material as claimed in claim 1 and a tricalcium phosphate powder; and
   an orally receivable carrier;
   wherein the powder of the calcium phosphate-based core-shell structured material and the tricalcium phosphate powder are mixed in a weight ratio from 3:5 to 3:7.

6. The oral care composition according to claim 5, wherein the oral care composition is a toothpaste, dental powder, tooth cleaning solution, mouthwash, mousse, denture product, topical oral gel, oral tablet, buccal tablet, sugar coated tablet, chewing gum, tooth patch, or dental brace in application.

7. The oral care composition according to claim 5, wherein the tricalcium phosphate powder is formed by sintering at a predetermined temperature between 700° C. and 1500° C.

8. The oral care composition according to claim 7, wherein the tricalcium phosphate powder is formed by a first sintering step and a second sintering step; wherein the first sintering step is performed at a temperature of 800° C. for 1 hour by heating at a temperature raising rate of 3° C./min, and the second sintering step is performed at a predetermined temperature between 1100° C. and 1200° C. for 1 to 3 hours by heating at a temperature raising rate of 5° C./min.

* * * * *